United States Patent
Halstead

(10) Patent No.: US 12,128,011 B2
(45) Date of Patent: Oct. 29, 2024

(54) THERAPEUTICALLY ADMINISTRABLE HIGH DOSE NON-AQUEOUS CURCUMINOID SOLUTIONS

(71) Applicant: Joseph Halstead, Singapore (SG)

(72) Inventor: Joseph Halstead, Singapore (SG)

( * ) Notice: Subject to any disclaimer, the term of this patent is extended or adjusted under 35 U.S.C. 154(b) by 687 days.

(21) Appl. No.: 17/310,429

(22) PCT Filed: Feb. 5, 2020

(86) PCT No.: PCT/AU2020/050081
§ 371 (c)(1),
(2) Date: Aug. 2, 2021

(87) PCT Pub. No.: WO2020/163899
PCT Pub. Date: Aug. 20, 2020

(65) Prior Publication Data
US 2022/0184001 A1    Jun. 16, 2022

(30) Foreign Application Priority Data

Feb. 11, 2019 (AU) .................. 2019900438

(51) Int. Cl.
*A61K 47/02* (2006.01)
*A61K 9/08* (2006.01)
(Continued)

(52) U.S. Cl.
CPC ................. *A61K 31/12* (2013.01); *A61K 9/08* (2013.01); *A61K 47/02* (2013.01); *A61K 47/10* (2013.01)

(58) Field of Classification Search
CPC .......... A61K 31/12; A61K 9/08; A61K 47/02; A61K 47/10; A61K 9/0019
See application file for complete search history.

(56) References Cited

U.S. PATENT DOCUMENTS

2009/0324703 A1    12/2009    Frautschy et al.

FOREIGN PATENT DOCUMENTS

| CN | 1895239 A | 1/2007 |
|---|---|---|
| CN | 102225048 A | 10/2011 |

(Continued)

OTHER PUBLICATIONS

Osada et al. Prediction of the solubility of organic compounds in high-temperature water using machine learning, vol. 190, 2022, 105733. (Year: 2022).*

(Continued)

*Primary Examiner* — Bruck Kifle
*Assistant Examiner* — Kevin S Martin
(74) *Attorney, Agent, or Firm* — INNOVATION CAPITAL LAW GROUP, LLP; Vic Lin

(57) ABSTRACT

A method involves dissolving a curcuminoid in glycerol to make an administrable solution. An alkali salt is added to the glycerol to increase the solubility of the curcuminoid in the glycerol to more than 20 milligrams curcuminoid per millilitre of glycerol (and up to in excess of 200 milligrams curcuminoid per millilitre of glycerol with the addition of sufficient alkali salt in embodiments). The resulting administrable solution can be administered (such as by way of intramuscular injection) as is without the need of an aqueous emulsion and can be stored for more titan 24 hours without curcuminoid precipitation.

23 Claims, 1 Drawing Sheet

(51) Int. Cl.
A61K 31/12 (2006.01)
A61K 47/10 (2017.01)
A61K 9/00 (2006.01)

(56) References Cited

FOREIGN PATENT DOCUMENTS

| CN | 103070825 A | 5/2013 |
| CN | 104585730 A | 5/2015 |
| JP | 2014101315 A | 6/2014 |
| JP | 2018533545 A | 11/2018 |
| WO | 2008042944 A2 | 4/2008 |
| WO | 2011002929 A1 | 1/2011 |
| WO | 2012146057 A1 | 11/2012 |
| WO | 2015086516 A1 | 6/2015 |

OTHER PUBLICATIONS

Subhashini, Chauhan PS, Kumari S, Kumar JP, Chawla R, Dash D, Singh M, Singh R. Intranasal curcumin and its evaluation in murine model of asthma. Int Immunopharmacol. Nov. 2013;17(3):733-43. doi: 10.1016/j.intimp.2013.08.008. Epub Sep. 8, 2013. PMID: 24021755. (Year: 2013).*

Sandur et al. Carcinogenesis. Aug. 2007;28(8):1765-73. doi: 10.1093/carcin/bgm123. Epub May 23, 2007. PMID: 17522064. (Year: 2007).*

Jain et al., American Institute of Chemical Engineers, Annual Meeting 2023, Abstract 472a, Solubility Prediction of Organic Molecules (Year: 2023).*

The Cambridge Dictionary, Proportional, 2024, https://dictionary.cambridge.org/us/dictionary/english/proportional (Year: 2024).*

Gao et al., "Preparation and characterization of intravenously injectable curcumin nanosuspension", Drug Delivery, 18:2 (2011); pp. 131-142.

International Preliminary Report on Patentability dated Jul. 15, 2020 from PCT Application No. PCT/AU2020/050081.

International Search Report & Written Opinion dated Mar. 3, 2020 from PCT Application No. PCT/AU2020/050081.

Kharat et al., Physical and Chemical Stability of Curcumin in Aqueous Solutions and Emulsions: Impact of pH, Temperature, and Molecular Environment:. Journal of Agricultural and Food Chemistry. J. Agric. Food Chem. 2017, 65, 1525-1532.

Marx et al., "Intranasal Drug Administration—An Attractive Delivery Route for Some Drugs", INTECH—Drug Discovery and Development—From Molecules to Medicine; Ch. 13; pp. 299-320, (2015).

Rodger et al., Drawing up and administering intramuscular injections: a review of the literature:. Journal of Advanced Nursing vol. 31, Issue 3, pp. 574-582 (2000).

Usach et al., Injection of Drugs: Literature Review of Factors Influencing Pain Sensation at the Injection Site:. Advances in Therapy. Nov. 2019, vol. 36, Issue 11, pp. 2986-2996.

* cited by examiner

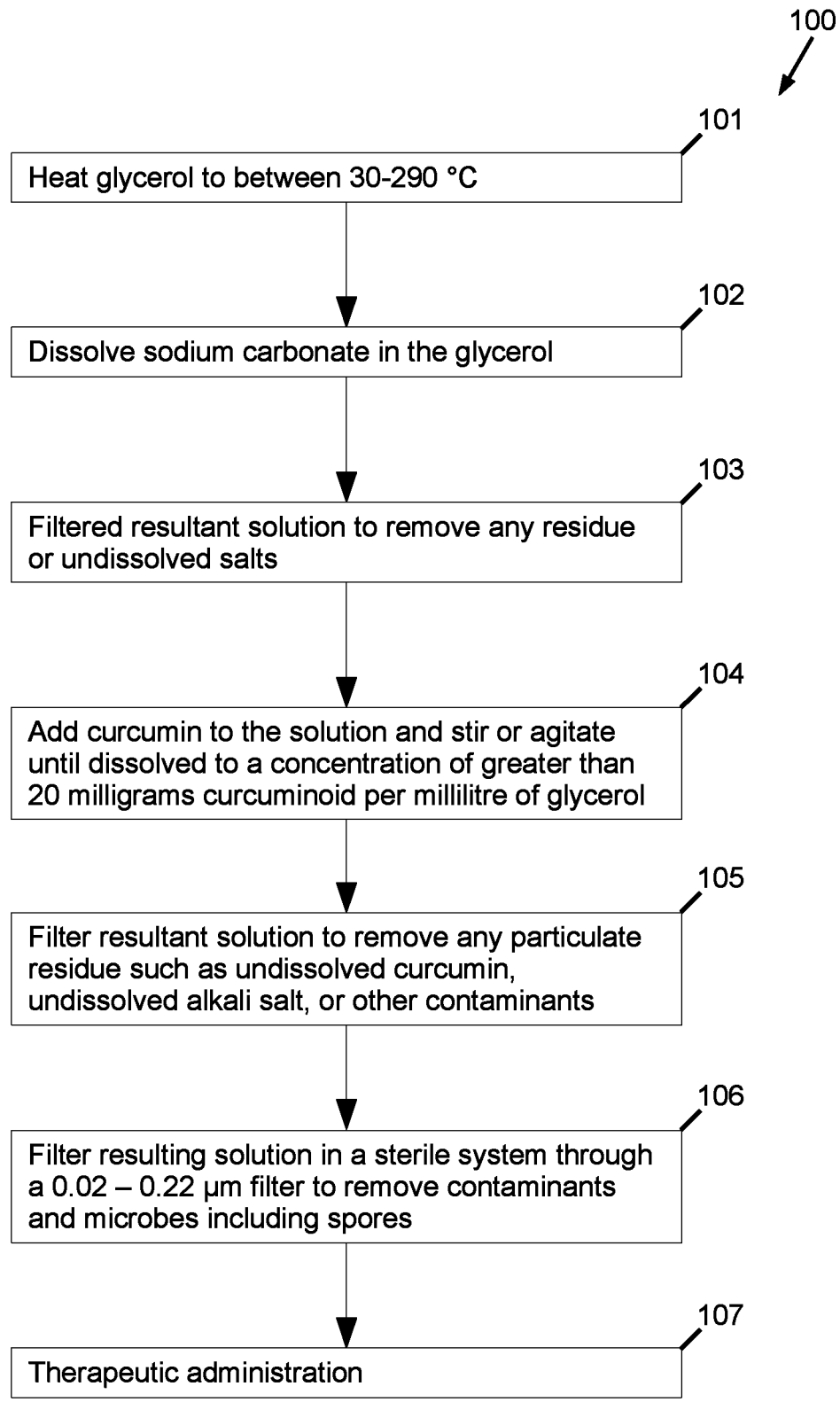

THERAPEUTICALLY ADMINISTRABLE HIGH DOSE NON-AQUEOUS CURCUMINOID SOLUTIONS

FIELD OF THE INVENTION

This invention relates generally to therapeutically administrable high dose non-aqueous curcuminoid solutions.

BACKGROUND OF THE INVENTION

Curcumin is a bright yellow chemical produced by some plants and is the principal curcuminoid of turmeric (*Curcuma longa*), a member of the ginger family, Zingiberaceae. Curcumin is a diarylheptanoid, belonging to the group of curcuminoids, which are natural phenols responsible for turmeric's yellow colour. The main curcuminoids include curcumin, demethoxycurcumin, bisdemethoxycurcumin and tetrahydrocurcumin.

Curcuminoids crystallise out of aqueous acidic solutions and degrade in alkaline aqueous solutions. For example, US20090324703A1 (Frautschy) 31 Dec. 2009 notes that curcumin is unstable in aqueous solutions above pH 7.0 where curcumin hydrolyzes to ferulic acid and vanillin breakdown products. Furthermore, according to *Physical and Chemical Stability of Curcumin in Aqueous Solutions and Emulsions: Impact of pH, Temperature, and Molecular Environment*. Journal of Agricultural and Food Chemistry. Kharat, Mahesh & Du, Zheyuan & Zhang, Guodong & Mcclements, David. (2016) 65. 10.1021/acs.jafc.6b04815, "Curcumin was highly unstable to chemical degradation in alkaline aqueous solutions (pH≥7.0) and tended to crystallize out of aqueous acidic solutions (pH<7)".

As such, administering injections of curcuminoids in water-based solutions is not practical. Furthermore, whereas curcuminoids are soluble in not aqueous solutions such as dimethyl sulfoxide (DMSO), acetone and ethanol and potentially in other organic solvents, ethanol however is painful and toxic when injected and DMSO is not generally used for injection, has been shown to be a neurotoxin in certain circumstances and causes an unpleasant odour for several hours post-injection.

WO 2012/146057 A1 (Chen et al.) 1 Nov. 2012 attempts to solve this problem by a two-stage process: firstly comprising preparing a curcumin solution with pH adjusting agents (lactic acid and sodium carbonate adjusting agents to adjust pH to maintain an acidic environment at a pH of 5.9) and a second stage wherein an alkali aqueous emulsion is added just prior use (or used within 18 hours of mixture).

For example, Example 4 of Chen teaches a mixture of curcumin in a solution of propylene glycol and glycerine and adjusted with pH adjusting agents comprising lactic acid and sodium carbonate to maintain an acidic environment at a pH of 5.9. Chen further teaches that the solution is to be mixed with an emulsion containing water preparation "at the time of use to prevent the precipitation of the curcuminoids during storage" to prevent crystallisation.

As such, Chen uses the pH adjusting agents to maintain an acidic environment to avoid degradation of the curcumin and adds aqueous emulsion just prior application to reduce the effects of precipitation.

However, problematically, the process taught by Chen requires addition of the aqueous emulsion just prior application to avoid precipitation and the solution taught by Chen therefore cannot be stored ready for use for more than 18 hour periods (see Chen, Abstract).

Other prior art relating to administration of curcuminoids similarly teach aqueous based solutions.

For example, WO 2015/086516A1 (Grahn et al) 18 Jun. 2015 claims a solution of glycerol in water, along with alkaline salts and curcumin for the purpose of manufacturing biodegradable aqueous lubricants. However, since Grahn requires water as part of the lubricant and dissolved curcumin, the solution taught by Grahn will be rapidly degraded in the hydrous alkaline environment. Furthermore, according to Grahn, the curcumin is only added as an antioxidant therefore the degradation of the curcumin will not necessarily negatively affect the antioxidant purpose of the invention. However, the solution taught by Grahn would not suitable for injection in humans.

Similarly, WO 2011/002929 A1 (Modak et al.) 6 Jan. 2011 teaches compositions of botanical ingredients, sometimes including curcuminoids, buffered to an acidic pH by lactic acid and sodium hydroxide, and comprising a minimum of 50% water by weight. However, as shown in Table 1 above, curcumin in not readily soluble in water or glycerol and is likely included in these various compositions as part of a topical cream, as opposed to for internal administration by injection.

Furthermore, WO 2008/042944 A2 (Modak) 10 Apr. 2008 teaches a composition for oral administration comprising 5 mg/ml curcuminoids and over 50% water, with no mention of pH. The compositions disclosed by Modak are neither intended nor suitable for internal administration by injection or any other means due to the addition of ingredients such as titanium dioxide which is not soluble in water and is highly toxic in a dose dependent manner when injected.

CN 104585730 A 6 May 2015 discloses solution of curcumin in water stabilised by first dissolving the curcumin in propylene glycol and acetic acid followed by raising the pH to 4-5 by addition of sodium acetate solution and then dilution with water in a ratio of 10:1 water to solution. The resultant solutions hold approximately 10-15 mg/ml at a pH of 4-5. Injection of acetic acid at a pH of 4-5 is extremely painful, and as such this solution is unsuitable for administration other than in food.

It may alternatively be possible to increase curcuminoid solubility or suspensibility in aqueous solutions with surfactants or co-surfactants, or to create emulsions or nanosuspensions of curcumin in non-aqueous solvents such as polyethylene glycol-200/400/600 or other organic solvents. For example, in *Preparation and characterization of intravenously injectable curcumin nanosuspension, Drug Delivery*, 18:2 Yan Gao et al. (2011), it is shown that nanoparticles of curcumin in suspension can be well tolerated compared to injections of curcumin prepared in PEG-400.

Furthermore, with reference to the following table, curcuminoids have poor solubility in water:

TABLE 1

| Water | 0.003 mg/ml |
|---|---|
| Glycerol | 0.80 mg/ml |
| Propylene glycol | 1.60 mg/ml |
| Polyethylene glycol 200 | 8.41 mg/ml |
| Polyethylene glycol 400 | 9.92 mg/ml |

Solubility of curcuminoids at neutral pH, from *Effect of hydrogen bond formation/replacement on solubility characteristics, gastric permeation and pharmacokinetics of curcumin by application of powder solution technology*; Authors Vijay Sharma, Kamla Pathak, Acta Pharmaceutica Sinica B Volume 6, Issue 6, November 2016

As such, Chen relies on Propylene glycol (see, for example, Example 4 of Chen) to increase the solubility of curcumin to approximately 1.5 mg/ml (see abstract of Chen).

However, as the maximum dose of intramuscular injection is 5 ml, the maximum dose for subcutaneous injection is 2 ml, the maximum dose for intranasal administration is 0.1 ml, and the maximum dose for suppository is 2 ml, the solution taught by Chen could only deliver relatively small doses of 7.5 mg, 3 mg, 0.15 mg or 3 mg respectively. (See for example, *Drawing up and administering intramuscular injections: a review of the literature*. Journal of Advanced Nursing Volume 31, Issue 3 Rodger, Michael A.; King, Lindy which states "injection into a large muscle group should not exceed 5 ml in adults"; *Subcutaneous Injection of Drugs: Literature Review of Factors Influencing Pain Sensation at the Injection Site*. Advances in Therapy. November 2019, Volume 36, Issue 11. Iris Usach Rafael MartinezTeodora FestiniJosé-Esteban Peris, which states that "the maximum volume generally accepted is around 1.5 ml, although volumes of up to 3 ml are well tolerated when injected in the abdomen." and *Drug Discovery and Development—From Molecules to Medicine*. Degenhard Marx, Gerallt Williams and Matthias Birkhoff. Published: Jun. 3, 2015. which states that "the anticipated [intranasal] dose should fit into a volume of roughly 100-200 µl").

Furthermore, curcuminoids are rapidly degraded, metabolised or excreted from the body to the extent that the peak plasma level after oral administration occurs within 1-2 hours. Curcumin administered via intravenous injection in rat models is typically 99% cleared from plasma within 1-24 hours after administration.

As such, as intravenous injection is only administrable in a clinical setting and since the administered curcuminoids will have been removed from the body within approximately 24 hours of administration, the solution having a dose of 1.5 mg/ml according to Chen would necessitate daily visits to a clinic or hospital.

As such, a need therefore exists for a non-aqueous, high dose, long shelf life (i.e., greater than 24 hours) curcuminoid solution which can be administered as is without the need of further preparation at the time of application.

It is to be understood that, if any prior art information is referred to herein, such reference does not constitute an admission that the information forms part of the common general knowledge in the art, in Australia or any other country.

SUMMARY OF THE DISCLOSURE

There is provided herein a method which comprises preparing a nonaqueous administrable curcuminoid solution, and more specifically, comprises dissolving a curcuminoid in glycerol. Glycerol is a non-aqueous solvent suitable for human consumption or injection. However, as outlined above, curcumin is barely soluble in glycerol.

Our experimentation found that curcumin unexpectedly becomes more readily soluble in glycerol with the addition of an alkali salt for reasons hitherto not yet fully understood, but probably because curcuminoids are typically weak acids.

As such, an alkali salt is added to the glycerol so that the curcuminoid dissolves to a concentration greater than those achievable using carriers such as Propylene glycol, Polyethylene glycol 200 and Polyethylene glycol 400 which, with reference to the above table, can only achieve maximum doses of approximately 10 milligram of curcuminoid per millilitre of solution. One alkali salt we found suitable was sodium carbonate although other alkali salts may be potentially use including calcium hydroxide and calcium carbonate.

For example, we found that adding 0.1 mg to 20 mg sodium carbonate per millilitre glycerol achieved concentrations of 0-300 mg curcumin per millilitre of glycerol.

As such, the present administrable solution allows for a dose of greater than 20 mg of curcuminoid per millilitre of glycerol (typically 20-250 mg of curcuminoid per millilitre of glycerol) which, for example, allows for a high dose intramuscular depot of solution which slowly dissolves in interstitial fluid and into the blood stream over the course of days/weeks, avoiding daily injections/clinic visits.

As such, in contradistinction with the prior art solutions, the present formulation is not aqueous, thereby avoiding problems of curcuminoid precipitation and degradation. Therefore, the present administrable solution can be stored for greater than 24 hours without precipitation or chemical degradation and need not be used within 18 hours as does the solution taught by Chen.

Furthermore, the present administrable solution can be applied directly as is without need for the prior addition of an aqueous emulsion.

The prior art, including Chen, does not teach or obviously suggest making a nonaqueous administrable solution of a curcuminoid and glycerol wherein an alkali salt is added to the glycerol to increase the solubility of the curcuminoid in the glycerol to more than 20 milligrams curcuminoid per millilitre of glycerol.

According to one aspect, there is provided a method comprising dissolving a curcuminoid in glycerol to make an administrable solution, wherein an alkali salt is added to the glycerol to increase the solubility of the curcuminoid in the glycerol to more than 20 milligrams curcuminoid per millilitre of glycerol, and therapeutic administration of the administrable solution.

An alkali salt may be added to the glycerol to increase the solubility of the curcuminoid in the glycerol to more than 20 milligrams curcuminoid per millilitre of glycerol, and therapeutic administration of the administrable solution.

More than 1 milligrams of alkali salt may be added to the glycerol.

The administrable solution may comprise a concentration of greater than 100 milligrams curcuminoid per millilitre of glycerol.

More than 6 milligrams of alkali salt may be added to the glycerol.

The administrable solution may comprise a concentration of approximately 200 milligrams curcuminoid per millilitre of glycerol.

More than 13 milligrams of alkali salt may be added to the glycerol.

The administrable solution may comprise a concentration of approximately 250 milligrams curcuminoid per millilitre of glycerol.

More than 16 milligrams of alkali salt may be added to the glycerol.

Administration may comprise administration of the administrable solution more than 24 hours after dissolving the curcuminoid in the glycerol.

Administration may comprise administration of the administrable solution as is.

Administration may comprise administration of the administrable solution without the addition of water.

The administrable solution may not comprise Propylene glycol or Polyethylene glycol.

The curcuminoid may be curcumin.

The curcuminoid may be at least one of a curcuminoid selected from the group consisting of curcumin, metabolites of curcumin, tetrahydrocurcumin, demethoxycurcumin, bisdemethoxycurcumin and curcumin esters.

The alkali salt may comprise sodium carbonate.

The alkali salt may comprise at least one of calcium hydroxide and calcium carbonate.

The method may further comprise heating the glycerol to between the melting and the boiling point of glycerol.

The method may further comprise filtering the curcuminoid solution to remove any undissolved alkali salt.

The method may further comprise allowing the curcuminoid solution to cool and filtering the curcuminoid solution to remove any undissolved or precipitated curcuminoid.

The method may further comprise antibacterial filtration of the curcuminoid solution through a 0.02-0.22 µm filter.

Administration may comprise injection.

Injection may comprise intramuscular injection.

Injection may comprise at least one of subcutaneous, intradermal, intraperitoneal and intra-abdominal injection.

Administration may comprise at least one of intranasal spray delivery, delivery using enteric coated capsules to bypass stomach acid and rectal or colonic delivery by suppository.

According to another aspect, there is provided an administrable solution comprising curcuminoid dissolved in glycerol, wherein an alkali salt is added to the glycerol so that the curcuminoid dissolves to a concentration of greater than 20 milligrams curcuminoid per millilitre of glycerol.

The administrable solution may comprise a concentration of approximately 200 milligrams curcuminoid per millilitre of glycerol and more than 13 milligrams of alkali salt may be added to the glycerol.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which:

FIG. 1 shows a method for making an administrable curcumin solution.

DESCRIPTION OF EMBODIMENTS

FIG. 1 shows a method 100 for preparation of an administrable curcumin solution in accordance with an embodiment. It should be noted that the method 100 is an exemplary embodiment of the method of preparation and variations may be made thereto within the purposive scope of the present invention.

The method 100 may comprise heating a glycerol to between the melting point and the boiling point (17° C. 290° C.) thereof at step 101.

At step 102, an alkali salt, such as sodium carbonate is dissolved in the heated solution of glycerol and alkali salt to raise the amount of curcumin that can be diluted in the glycerol to greater than 20 milligrams per millilitre of glycerol.

Step 103 may entail filtering the resultant solution to remove any residue and/or any undissolved salts.

Step 104 comprises the addition of a curcuminoid (such as curcumin) to the solution and stirring or otherwise mixing or agitating the solution until the curcuminoid is partially or substantially dissolved. In alternative embodiments, the curcuminoid may be added prior the addition of the alkali salt. In alternative embodiments, the curcuminoid may comprise metabolites of curcumin, tetrahydrocurcumin, demethoxycurcumin, bisdemethoxycurcumin, curcumin esters and mixtures thereof.

We found that addition of approximately between 0.1-20 mg of sodium carbonate or more per millilitre of glycerol results in the solubility of a corresponding ratio of approximately 0-300 mg of curcumin or more per millilitre of glycerol. Both sodium carbonate and curcumin can be used at higher concentrations if required.

Step 105 may comprise filtering the resultant solution to remove any particulate residue such as undissolved curcumin or undissolved alkali salt, or other potential contaminants.

Step 106 may comprise filtering the resultant solution in a sterile system, such as through a 0.02-0.22 µm filter, to remove any contaminants and microbes including spores, or any other suitable method to sterilise the solution including pre-filtration of the glycerol, pre-filtration of the curcumin while dissolved in ethanol followed by evaporation of the ethanol, heat sterilisation of individual or combined ingredients, or ultra-violet sterilisation.

Step 107 may comprise the therapeutic administration/human application of the prepared solution, such as by way of injection.

Injection may comprise intramuscular injection, but in embodiments, may also comprise subcutaneous, intradermal, intraperitoneal and intra-abdominal injection.

The solution may alternatively be delivered as an intranasal spray, potentially with the addition of thinners to the solution or with the use of an atomiser.

The solution may also be used to create a nano-suspension suitable for administration via injection by mixing with water or other antisolvent prior to injection which may cause the curcumin to precipitate out of solution as very fine particles in suspension. The solution may also be used in suppositories or enteric coated capsules for intestinal use, or potentially increased absorption into the liver or bloodstream via absorption in the intestines.

In accordance with a preferred embodiment, the human administrable curcuminoid solution may comprise:

1—Glycerol;
2—An alkali salt or compound that can dissolve in the glycerol and not react excessively with curcumin or the solvent such as sodium carbonate;
3—a curcuminoid (including curcumin, metabolites of curcumin, tetrahydrocurcumin, demethoxycurcumin, bisdemethoxycurcumin, curcumin esters, and mixtures thereof); and
4—a preservative or preservatives in embodiments (or anti-fungal or anti-bacterial agent such as benzoic acid which is soluble in glycerol.)

Whereas sodium carbonate may be suitable because of the relatively high solubility thereof in glycerine, sodium carbonate may raise the pH of the surrounding tissue when injected, especially for correspondingly high dose ratio curcumin solutions. As such, possible suitable alternatives include calcium hydroxide, calcium carbonate or any alkaline salt of glycerol, or any alkali molecule that is soluble in a suitable non-aqueous solvent.

Furthermore, because the prepared solution may be relatively viscous, especially for high dose solutions, the solution may be treated prior injection to reduce the viscosity thereof. Such may include warming the solution prior to injection or addition of a diluent prior to injection or during the manufacturing process. Preferably, the diluent comprises less than 50% volume of the injected solution.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method to make an administrable solution having a concentration of a curcuminoid of more than 100 mg/mL, the method comprising:
adding an alkali salt to glycerol, wherein the alkali salt is added proportionately per millilitre of the glycerol to increase the solubility of the curcuminoid in the glycerol; and
dissolving, in the glycerol, more than 100 milligrams of the curcuminoid per millilitre of the glycerol,
wherein the curcuminoid is at least one of a curcuminoid selected from the group consisting of curcumin, tetrahydrocurcumin, demethoxycurcumin, bisdemethoxycurcumin and mixtures thereof.

2. A method as claimed in claim 1, wherein more than 1 milligrams of alkali salt is added to the glycerol.

3. A method as claimed in claim 1, wherein more than 6 milligrams of alkali salt is added to the glycerol.

4. A method as claimed in claim 1, wherein the administrable solution comprises a concentration of approximately 200 milligrams curcuminoid per millilitre of glycerol.

5. A method as claimed in claim 4, wherein more than 13 milligrams of alkali salt is added to the glycerol.

6. A method as claimed in claim 1, wherein the administrable solution comprises a concentration of approximately 250 milligrams curcuminoid per millilitre of glycerol.

7. A method as claimed in claim 6, wherein more than 16 milligrams of alkali salt is added to the glycerol.

8. A method as claimed in claim 1, further comprising administrating the administrable solution more than 24 hours after dissolving the curcuminoid in the glycerol.

9. A method as claimed in claim 1, further comprising administrating the administrable solution without the addition of water.

10. A method as claimed in claim 1, wherein the administrable solution does not comprise Propylene glycol or Polyethylene glycol.

11. A method as claimed in claim 1, wherein the curcuminoid is curcumin.

12. A method as claimed in claim 1, wherein the alkali salt comprises sodium carbonate.

13. A method as claimed in claim 1, wherein the alkali salt comprises at least one of calcium hydroxide and calcium carbonate.

14. A method as claimed in claim 1, further comprising heating the glycerol to between the melting and the boiling point of glycerol after adding the alkali salt to the glycerol.

15. A method as claimed in claim 14, further comprising filtering the curcuminoid solution to remove any undissolved alkali salt.

16. A method as claimed in claim 14, further comprising allowing the curcuminoid solution to cool and filtering the curcuminoid solution to remove any undissolved or precipitated curcuminoid.

17. A method as claimed in claim 1, further comprising antibacterial filtration of the curcuminoid solution through a 0.02-0.22 µm filter after dissolving more than 20 milligrams of the curcuminoid per millilitre of the glycerol.

18. A method as claimed in claim 1, further comprising administrating the administrable solution by injection.

19. A method as claimed in claim 18, wherein injection comprises intramuscular injection.

20. A method as claimed in claim 18, wherein injection comprises at least one of subcutaneous, intradermal, intraperitoneal and intra-abdominal injection.

21. A method as claimed in claim 1, further comprising administering the administrable solution by at least one of intranasal spray delivery, delivery using enteric coated capsules to bypass stomach acid and rectal or colonic delivery by suppository.

22. An administrable solution comprising:
an alkali salt in glycerol, wherein the alkali salt is added proportionately per millilitre of the glycerol to increase the solubility of a curcuminoid in the glycerol; and, in the glycerol, more than 100 milligrams of the curcuminoid is dissolved per millilitre of glycerol,
wherein the curcuminoid is at least one of a curcuminoid selected from the group consisting of curcumin, tetrahydrocurcumin, demethoxycurcumin, bisdemethoxycurcumin and mixtures thereof.

23. An administrable solution as claimed in claim 22 wherein the administrable solution comprises a concentration of approximately 200 milligrams curcuminoid per millilitre of glycerol and wherein more than 13 milligrams of alkali salt is added to the glycerol.

* * * * *